United States Patent
Sauvant-Moynot et al.

(10) Patent No.: US 6,842,016 B2
(45) Date of Patent: Jan. 11, 2005

(54) METHOD OF EVALUATING THE TIME LEFT BEFORE GELATION OF A THERMOSETTING COMPOSITION

(75) Inventors: Valérie Sauvant-Moynot, Lyons (FR); Sébastien Duval, Evron (FR); Sylvie Schweitzer, Villette de Vienne (FR); Dominique Audigier, Vourles (FR)

(73) Assignee: Institut Francais Du Petrole, Rueil Malmaison Cedex (FR)

( * ) Notice: Subject to any disclaimer, the term of this patent is extended or adjusted under 35 U.S.C. 154(b) by 129 days.

(21) Appl. No.: 10/274,997

(22) Filed: Oct. 22, 2002

(65) Prior Publication Data

US 2003/0080758 A1 May 1, 2003

(30) Foreign Application Priority Data

Oct. 26, 2001 (FR) .............................................. 01 14080

(51) Int. Cl.[7] .............................................. G01R 27/26
(52) U.S. Cl. ........................ 324/663; 324/71.1; 324/676
(58) Field of Search ................................ 324/663, 676, 324/71.1

(56) References Cited

U.S. PATENT DOCUMENTS

| | | | |
|---|---|---|---|
| 4,777,431 A | * 10/1988 | Day et al. .................... 324/690 |
| 5,210,499 A | 5/1993 | Walsh | |
| 5,219,498 A | * 6/1993 | Keller et al. ................. 264/408 |
| 5,432,435 A | * 7/1995 | Strong et al. ............... 324/71.1 |
| 5,525,155 A | * 6/1996 | Allen .......................... 106/802 |
| 5,530,369 A | * 6/1996 | Kleinmeyer ................. 324/676 |
| 5,680,055 A | * 10/1997 | Seitz et al. .................. 324/715 |
| 5,872,447 A | * 2/1999 | Hager, III .................. 324/71.1 |
| 5,898,309 A | 4/1999 | Becker et al. | |
| 6,577,958 B1 | * 6/2003 | Green et al. .................. 702/45 |

FOREIGN PATENT DOCUMENTS

| | | |
|---|---|---|
| DE | 4120573 | 12/1992 |
| DE | 19601947 | 9/1997 |
| EP | 0542508 | 5/1993 |
| FR | 2645275 | 10/1990 |
| WO | 9859151 | 12/1998 |

* cited by examiner

Primary Examiner—Charles H. Nolan, Jr.
(74) Attorney, Agent, or Firm—Antonelli, Terry, Stout & Kraus, LLP

(57) ABSTRACT

Non-destructive method allowing in-situ evaluation, in a sensitive and reproducible way, for a given thermosetting composition, of the time left before gelation of said composition as a function of a quantity measuring its dielectric behavior.

14 Claims, 2 Drawing Sheets

METHOD OF EVALUATING THE TIME LEFT BEFORE GELATION OF A THERMOSETTING COMPOSITION

FIELD OF THE INVENTION

The present invention relates to a non-destructive method allowing in-situ evaluation, from dielectric measurements, of the residual gel time of thermosetting compositions such as paints or resins, typically after a <<pot life>> period. In the present description, <<pot life>> is understood to be a period during which all of the events preceding a stage of curing of said compositions leading to the gelation thereof occur, said stages being, for example, drum storage, fiber impregnation according to a technique well-known to the man skilled in the art as Resin Transfer Molding (RTM), storage and setting of prepregs or, in general, any heating stage preceding said curing stage.

More precisely, the invention relates, for a given thermosetting composition, to a method allowing to evaluate, in a sensitive and reproducible way, the residual gel time of said composition as a function of a quantity measuring the dielectric behaviour of said composition, said quantity being for example the impedance or any other physical variable equivalent thereto or deducible therefrom by the man skilled in the art.

BACKGROUND OF THE INVENTION

The <<pot life>> of a thermosetting composition is in most cases accompanied by the onset of an unwanted polymerization reaction of said composition. This polymerization reaction onset is often disregarded in relation to the polymerization reaction occurring during the final curing stage, for example for a well tubing or a pipe. Now, this thermosetting composition curing stage is conditioned by the time left before gelation of said composition (this time is referred to in the description hereafter as <<residual gel time>> under the temperature conditions of said implementation. In fact, the gelation of a thermosetting composition, i.e. the change from the viscous liquid state to the viscoelastic solid state, marks an irreversible change in its rheological behaviour, its viscosity becoming infinite then. Gelation can also be defined by the following change: before gelation, the composition is soluble in a solvent consisting of the initial monomers, and after gelation the composition is no longer soluble in this solvent. Since the viscosity rise is relatively sudden at the approach of the gel point, the specialist's knowledge of the residual gel time during the pot life is critical as regards the applications considered. For example, in the case of resins intended for impregnation of fiber mats for composite parts, the residual gel time of the thermosetting composition is often defined for controlled temperature conditions. If any deviation from these conditions occurs, the thermal history of the drums can no longer be controlled: the residual gel time of the thermosetting composition is no longer accessible and the viscosity properties for impregnation are no longer controlled, which is harmful to the impregnation process. In an extreme case, the residual gel time may be too short for the application considered. Thus, in the case of flexible preforms pre-impregnated with polymerizable resin intended for the inner lining of wells, as described in patent application WO-98/59,151, setting of the lining on the well walls by radial deformation towards the outside is conditioned by the viscosity of the polymerizable resin, which depends on the progress stage of the polymerization reaction. Above the gel point, the preform loses its flexibility and cannot be applied by radial deformation on the well walls. It is thus impossible to use the thermosetting resin, conditioned by the progress of the polymerization, above the gel point.

Control of the use of thermosetting compositions therefore requires consideration of the thermal history preceding this use.

The conventional gel time measuring methods are based on rheological measurements which follow the evolution with time of the dynamic shear moduli G' and G" (Winter H. H., Polymer Engineering and Science, 1987, Vol.27, 1698–1702). Certain rudimentary devices detecting an infinite viscosity increase by means of a mobile body moved in the thermosetting composition give satisfactory measurements of the residual gel time, but all these equipments involve sampling. Now modern industrial practices very often use non-destructive material evaluation techniques which ideally allow to monitor and to control certain properties in-situ, i.e. while the materials are used.

Dielectrometry has thus emerged as a prime non-destructive technique allowing real-time monitoring of the evolution of the dielectric properties of thermosetting compositions during polymerization, in particular during curing stages and use of pure or composite resins, on the laboratory scale as well as on the industrial scale (Stéphan F., Boiteux G., Seytre G., Ulanski J., J. Non Crystalline Solids, 1994, Vol.172–174, pp.1001–1011). It is well-known that a network develops progressively through linear growth, branching and crosslinking leading to the formation of molecular species of ascending size. As regards the dielectric response of the material, polymerization manifests itself for example in a decrease in the conductivity measured in the medium. Correlating a conductivity calculated from the loss factor with the degree of polymerization of the material has also been proposed (Kranbuehl D. E., Processing of Composites, pp.137–157, Hanser Ed., 2000), as well as using the real and imaginary parts of the complex impedance of epoxy-amine resins cured at high temperatures to calculate the resistivity of the resin and to correlate it with the progress of the reaction, i.e. the crosslinking degree of the network (Mijovic J., Yee C. F. W., Macromolecules, 1994, Vol.27, pp.7287–7293). It is furthermore well-known that dielectric measurements can also be correlated with certain physical properties of the resin such as its viscosity before the gel point.

It is however admitted that dielectric measurements (assembled under the generic term dielectrometry) cannot provide a direct measurement of the residual gel time of a resin under given temperature conditions, since the gelation of a thermosetting composition induces no particular signature on said dielectric measurements (Eloundou J. P., Gérard J. F., Pascault J. P., Boiteux G., Seytre G., Die Angewandte Makromolekulare Chemie, 1998, Vol.263, pp.57–70). In fact, the gelation of a thermosetting composition is defined by a chain growth degree such that a macromolecule of infinite size has formed. At gel point, the formation of a non densely crosslinked 3D network structure is therefore not a sensitive disturbance on the dipoles and charge carriers scale.

Surprisingly enough, the applicant has however found that it is possible to correlate by dielectrometry, for a given temperature, the residual gel time of a thermosetting composition at any time whatever the thermal history of said composition, and more particularly during or after its pot life, or during its use.

SUMMARY OF THE INVENTION

In general terms, the invention relates to a method of evaluating the time left before gelation of a sample of a thermosetting composition during the polymerization reaction, wherein the following stages are carried out:

a) drawing, by means of dielectric measurements performed on the composition, a first chart representing the critical frequency associated with a predetermined value $\phi$ of the phase shift as a function of the temperature of the composition and as a function of the progress of the polymerization reaction of the composition, b) drawing a second chart representing the time left before gelation of the composition as a function of the temperature of the composition and as a function of the progress of the polymerization reaction of the composition, c) at a time t1, determining the critical frequency associated with said phase shift value $\phi$ by means of dielectric measurements performed on a sample of the composition under polymerization and measuring the temperature T of the sample, d) by means of the first chart, of the critical frequency determined in stage c) and of temperature T measured in stage c), determining the progress stage of the polymerization reaction of the composition of the sample at the time t1, e) by means of the second chart and of the progress stage determined in stage d), determining the time left before gelation of the composition of the sample after the time t1 as a function of the temperature to which the sample will be subjected after the time t1.

In stages a) and c), dielectric measurements can be performed by contacting two electrodes with the composition, by applying an alternating electric potential to the composition placed in the air gap of the electrodes and by measuring the alternating current developed in the air gap so as to calculate the complex impedance.

According to the invention, the following stages can be carried out in stage a):

1) measuring the progress of the polymerization reaction of the composition as a function of time and of the temperature of the composition, 2) measuring the complex impedance of the composition as a function of time, as a function of the temperature of the composition and of the frequency of the electric potential, 3) by means of the measurements of stage 2), calculating the phase shift between the electric potential and the current as a function of time, of the temperature of the composition and of the frequency of the electric potential, 4) by means of stage 3), determining the critical frequency associated with said phase shift value $\phi$ as a function of time and of the temperature of the composition, 5) drawing the first chart by means of the measurements performed in stage 1) and of the critical frequency determined in stage 4).

In stage 4), the critical frequency curve can be adjusted by means of a parameterized equation from a circuit equivalent to a resistor mounted in parallel with a capacitor.

According to the invention, the following stages can be carried out in stage b):

6) measuring the progress of the polymerization reaction of the composition as a function of time and of the temperature of the composition, 7) measuring the time left before gelation of the composition as a function of the progress of the polymerization reaction of the composition and of the temperature of the composition, 8) drawing the second chart with the measurements obtained in stages 6) and 7).

According to the invention, the following stages can be carried out in stage c):

9) measuring the complex impedance of the sample as a function of the frequency of the electric potential at the time t1, 10) by means of the measurements of stage 9), determining the critical frequency associated with said value $\phi$ of the phase shift between the electric potential and the current, 11) measuring the temperature T of the sample at the time t1.

In stages 1 and 4, the progress of the polymerization reaction can be measured by means of one of the following methods: differential enthalpy, infrared spectroscopy, steric-exclusion chromatography and NMR. In stage 7), the gelation of the composition can be determined by rheology.

According to the invention, said value $\phi$ of the phase shift is $-45°$.

The method according to the invention can be used to determine the time left before gelation of a tubular preform pre-impregnated with polymerizable resin, the preform being intended to be installed in an oil well, then to be applied on the well walls by radial deformation.

BRIEF DESCRIPTION OF THE FIGURES

Other features and advantages of the invention will be clear from reading the description hereafter of a non-limitative embodiment of the present method, with reference to the accompanying drawings wherein.

DETAILED DESCRIPTION

Figure 1:
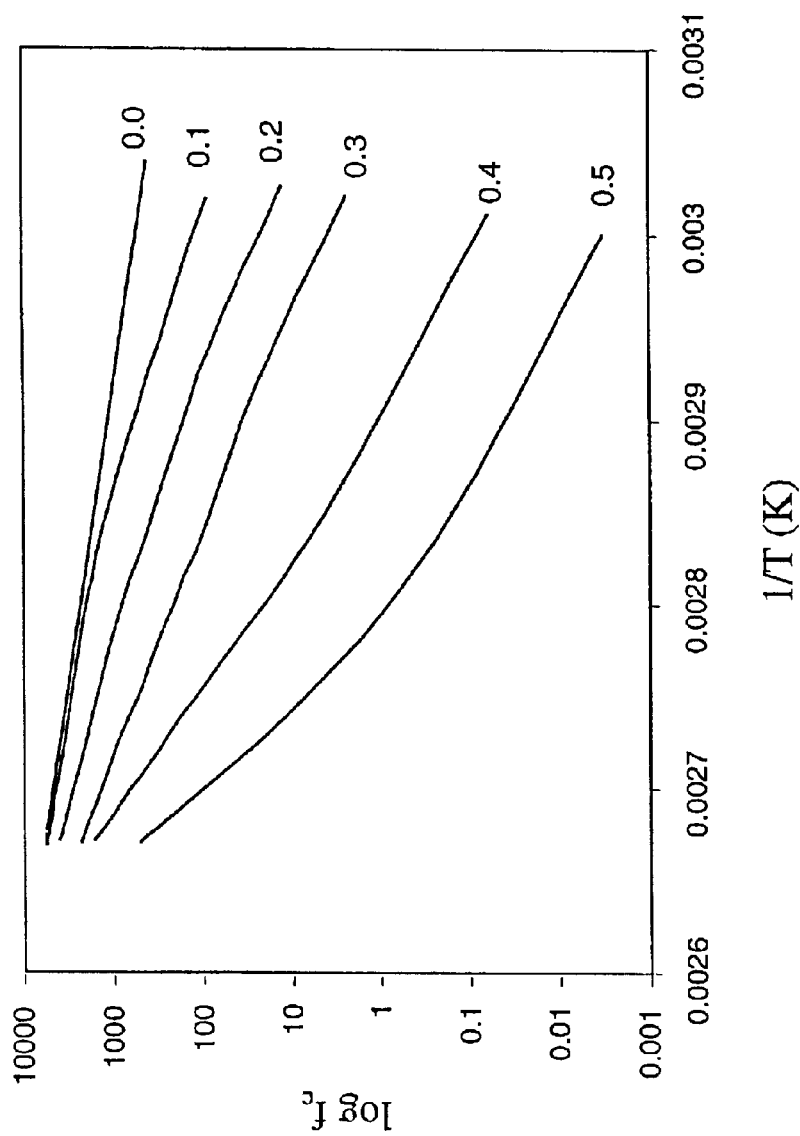
FIG. 1 shows the evolution of the critical frequency as a function of the inverse of the temperature at various progress stages of the reaction.

According to the invention, there are two phases to the method of evaluating the residual gel time of a thermosetting composition:

to start with, an initial study of the thermosetting composition carried out in the laboratory allows charts to be drawn, then, application of said charts allows to determine immediately, in a simple and non-destructive way, by means of a simple dielectric measurement, the residual gel time of any sample of said thermosetting composition before or during the use of said sample under the temperature conditions of said use.

Drawing the Charts

A first chart is made to connect various progress stages of the polymerization reaction to dielectric measurements. The method used to perform the dielectric measurements is preferably selected according to the invention so as to be applicable in the laboratory as well as for in-situ measurements for example on prepregs or composite parts used in particular in the petroleum sphere.

Thus, according to an embodiment of the present method, measurements of the progress stage of the polymerization reaction of the composition at different isotherms as a function of time are performed by means of a conventional method (such as, for example, differential enthalpic analysis (DSC), infrared spectroscopy, steric-exclusion chromatography or NMR (nuclear magnetic resonance)). These measurements are carried out from the start of the polymerization reaction at least to the gel point of the composition.

For the same isotherms, dielectric measurements are performed as a function of time. These measurements are also performed from the start of the polymerization reaction up to after the gel point of the composition.

Correlation between the measurements performed by means of a conventional method and the measurements performed by dielectrometry allows to draw a first chart specific to the composition studied which records, as a function of the temperature at which said measurements are performed, the dielectric measurements for different progress stages of the reaction.

Preferably, said dielectric measurement is a dynamic measurement of the components of the complex impedance of the material ($Z^*=Z'+iZ''$, with $Z'$ real part of the impedance and $Z''$ imaginary part of the impedance) performed by dielectric detectors. The complex impedance allows to calculate the phase shift between the potential applied to the resin and the resulting current: phase shift $\phi=\arctan(Z''/Z')$. Thus, at constant temperature, the frequency measurements of $Z'$ and $Z''$ allow for example to calculate the frequency dependence of the phase shift $\phi=\arctan(Z''/Z')$. This curve is advantageously adjusted by a parameterized equation from a simple R-C type (resistor-capacitor) equivalent circuit in parallel in order to determine the critical frequency <<fc>> associated with a phase shift of $-45°$ for example. According to the invention, the value of the phase shift between the potential and the current can range between $0°$ and $-90°$. In practice, said phase shift can be obtained for example by applying, by means of electrodes, a potential difference on the resin and by measuring the induced current, or by applying a current density and by measuring the induced potential. This frequency <<fc>> can be typically taken as the reflection of the progress of the polymerization reaction. Of course, the selection of the critical frequency <<fc>> such as described above is only given by way of example and any other quantity or any other parameter associated with or deducible from the initial dielectric measurements can be selected by the man skilled in the art without departing from the scope of the invention.

The dielectric measurements are preferably performed with an impedance analyzer connected to two electrodes and controlled by a computer. The impedance analyzer applies to the polymer material placed in the air gap of the two electrodes an alternating electric field generally in a frequency range of at least six decades. According to the present example, the measurement of the alternating current developed in the air gap of the two electrodes allows to calculate the complex impedance $Z^*$ of the material which serves as a basis for calculation of the phase shift $\phi=\arctan(Z''/Z')$.

A second chart is drawn to record the progress of the polymerization reaction as a function of the residual gel time of said thermosetting composition. The gel time of the composition is therefore measured by means of a known rheology method from the initial state (corresponding to a substantially zero progress of the polymerization reaction) and for the same isotherms as before. It is also possible according to the invention to measure the residual gel time of various samples of said resin with known progress stages of the polymerization reaction as a function of the same isotherms. In an alternative embodiment of the invention, it is possible to deduce from the measurement in the initial state residual gel times in relation to different progress stages of the polymerization reaction. This deduction can be made for example according to reaction kinetics data that is already known.

The correlation between said rheology measurements and the measurements of the progress of the reaction as a function of time performed upon drawing the first chart allows to draw a second chart, also specific to the resin studied, which records the residual gel time associated with the progress of the reaction as a function of the temperature conditions applied to the resin during use.

Use of the Charts

In order to know the residual gel time of a thermosetting resin of a given type after a pot life, a multifrequency measurement, at constant and known temperature, of the complex impedance is carried out on a sample. The phase shift curve $\phi=\arctan(Z''/Z')$ is then calculated as a function of the frequency in order to determine the critical frequency <<fc>> associated with phase shift $\phi$ used to draw the first chart ($\phi$ ranging between $0°$ and $-90°$, for example $-45°$).

Considering the first chart previously drawn according to the method described above for this type of resin, the man skilled in the art can know, in a non-destructive, simple and immediate way, the progress of the polymerization reaction of the sample considered.

The use of a second chart (also previously drawn according to the method already described) allows to evaluate, by means of the progress determined with the first chart, the time left before gelation of the sample of the resin considered as a function of the temperature to which the sample will be subjected afterwards.

The present method thus affords the advantage of evaluating, at any time, the progress of the polymerization reaction and the time left before gelation of a thermosetting resin without influencing, because of the technique involved, the measurement performed. This method is particularly well-suited for determination of the residual gel time of a thermosetting resin used in prepreg form or in a multilayer composite structure. In fact, the method proposed does not involve removal of the material from the medium and it does not modify the polymerization, and therefore the value of the residual gel time, in any way. Advantageously, the detector allowing the dielectric measurement to be performed is inserted in the resin considered so as to be able to know, continuously or intermittently, the residual gel time whatever the temperature variations applied to said resin. In most cases, a known temperature measuring device such as a thermocouple can be associated with said detector.

All the known thermosetting resins, pure or in admixture, and by extension these resins as composite matrices or in the presence of various fillers such as, for example, titanium dioxide, iron oxide, carbonates, silicates, barium sulfates, mica, clays, can be characterised by the method which is the object of the present invention. The compositions obtained from a mixture of a thermosetting resin and of a thermoplastic resin can also be characterised by the method according to the present invention.

The electrodes and their layout are designed not to disturb noticeably the polymerization; electrodes known to the man skilled in the art with an interdigital comb configuration are preferably selected. According to the invention, precise knowledge of the geometry of the electrode device is not essential because the present method is based, at a fixed temperature, on an adjustment of the dielectric phase shift data by a parameterized equation allowing to determine the critical frequency associated with a −45° phase shift. Advantageously, said phase shift being the ratio of the real and imaginary parts of the impedance, the multifrequency dielectric permittivity data are calculated to within a constant and they therefore do not influence said phase shift.

The electrodes can consist of any inert conducting material, metal, metal alloy or conducting polymer, providing that the durability of the constituent material does not disturb the measurements. The deposit thickness of said conducting material is not critical for the invention and it generally ranges between 50 nanometers and 1 millimeter. The metal electrodes can be made of platinum or gold for example. The conducting polymers likely to be used as electrodes are, for example, doped polytetrafluoroethylene, polyvinyl carbazole, ferrocene-based polymers and silicones or other organic polymers/resins containing electrically conducting additives (graphite fillers for example). Good adhesion between the electrode and the substrate is desirable in order to limit parasitic polarization phenomena at the electrodes. This adhesion is obtained for example by metallizing the electrode under secondary vacuum, or by inserting a commercial push-broom sensor in contact with the non-polymerized resin.

Figure 2:
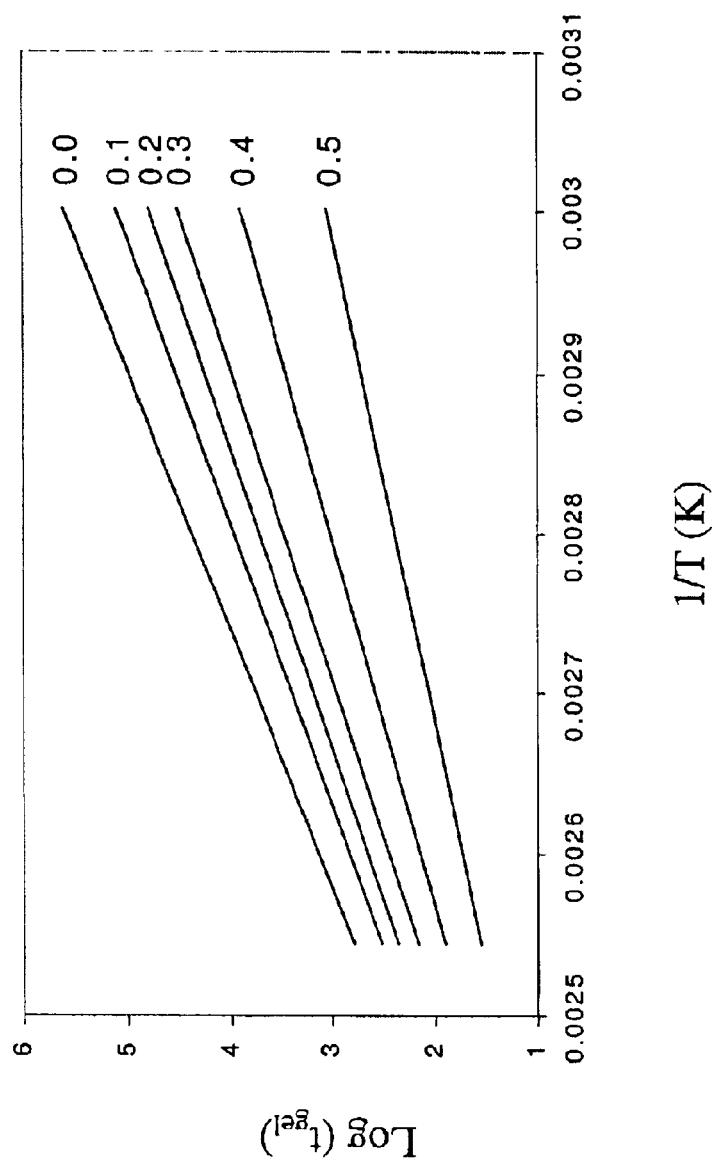
FIG. 2 shows the evolution of the time left before gelation as a function of the inverse of the temperature at various progress stages of the reaction.

By way of example for the present invention, FIGS. 1 and 2 show charts drawn by the applicant from measurements performed on a DGEBA-DDM resin. Said resin is obtained according to the rules through initial mixing (corresponding to a zero progress of the polymerization reaction) of the following precursors:

diepoxide DGEBA (diglycidyl ether bisphenol-A), diamine DDM (diamino-diphenyl methane).

The two precursors are mixed together so as to obtain a stoichiometric ratio of the reactive functions involved.

At first, kinetic studies carried out by infrared spectroscopy for different isotherms allow to establish, as a function of time, the progress of the polymerization reaction at different isotherms between 60° C. and 120° C.

For the same isotherms, according to the present method, multifrequency measurements of the complex impedance as a function of time are performed by contacting electrodes with the resin.

For each temperature, a critical frequency associated with a −45° phase shift between the potential applied to the resin and the current resulting from said application is determined on the basis of a R-C circuit model. Chart No. 1 shown in FIG. 1, which gives the evolution of the critical frequency as a function of the inverse of the temperature at various progress stages (from 0 to 0.5 in FIG. 1), is then drawn.

At the same time, the gel point of said resin is measured between 60° C. and 120° C. in the initial state (i.e. with a zero progress) and for various progress stages of the reaction. This measurement is performed over time with an equipment measuring the viscosity increase by means of a mobile body moved in the resin. A chart No. 2 is deduced from the experimental points obtained and from the kinetic studies carried out by spectroscopy. FIG. 2 thus shows, at different progress stages between 0 and 0.5, the evolution of the residual gel time of the resin (given in minutes) as a function of the inverse of the temperature.

Charts 1 and 2 thus form a set of data on the resin considered. It is possible to know, from this data set, the state of the polymerization reaction of any sample of this resin. Carrying out a multifrequency dielectric measurement and measuring the temperature of the sample is sufficient. This information allows to know, by means of the data contained in the first chart, the progress of the polymerization of the sample. Then, by means of the progress stage and of the second chart, the time left before gelation of the sample is determined.

For example, the invention allows to test a resin stored in drums in order to know if it can still be used or not. The progress of the polymerization reaction of the resin can be known by means of the method according to the invention. If a low progress stage is observed, the resin stored in drums can still be used, but if a high progress stage is determined, the resin is no longer usable.

Another application of the invention consists in knowing the time left during which a thermosetting resin part can be deformed, for example in the case of a flexible preform pre-impregnated with a polymerizable resin intended for the inner lining of a well. The pre-impregnated flexible (tubular) preform is first installed in the well. The preform is then applied against the walls of the well by radial deformation. In order to be able to achieve deformation of the preform, it is essential that the resin has not gelled yet. The method according to the invention allows, on the one hand, to check that the resin has not gelled yet and, on the other hand, to know the time left before gelation in order to organize setting of the preform.

Another application of the invention consists in optimizing the curing conditions of a thermosetting resin part so as to reach the gel point at the minimum. A thermosetting resin part is formed by moulding, casting, fiber coating or another technique. The present invention allows to estimate the curing time and temperature so as to obtain the desired polymerization degree.

What is claimed is:

1. A method of evaluating the time left before gelation of a sample of a thermosetting composition during the polymerization reaction, wherein the following stages are carried out:

a) drawing, by means of dielectric measurements performed on the composition, a first chart representing the critical frequency associated with a predetermined phase shift value $\phi$ as a function of the temperature of the composition and as a function of the progress of the polymerization reaction of the composition, b) drawing a second chart representing the time left before gelation of the composition as a function of the temperature of the composition and as a function of the progress of the polymerization reaction of the composition, c) at a time t1, determining the critical frequency associated with said phase shift value $\phi$ by means of dielectric measurements performed on a sample of the composition under polymerization and measuring the temperature T of the sample, d) by means of the first chart, of the critical frequency determined in stage c) and of temperature T measured in stage c), determining the progress of the polymerization reaction of the composition of the sample at the time t1, e) by means of the second chart and of the progress determined in stage d), determining the time left before gelation of the composition of the sample after the time t1 as a function of the temperature to which the sample will be subjected after the time t1.

2. A method as claimed in claim 1 wherein, in stages a) and c), dielectric measurements are performed by contacting two electrodes with the composition, by applying an alternating electric potential to the composition contained in the air gap of the electrodes and by measuring the alternating current developed in the air gap so as to calculate the complex impedance.

3. A method as claimed in claim 2 wherein, in stage a), the following stages are carried out:
- a1) measuring the progress of the polymerization reaction of the composition as a function of time and of the temperature of the composition,
- a2) measuring the complex impedance of the composition as a function of time, as a function of the temperature of the composition and of the frequency of the electric potential,
- a3) by means of the measurements of stage a2), calculating the phase shift between the electric potential and the current as a function of time, of the temperature of the composition and of the frequency of the electric potential,
- a4) by means of stage a3), determining the critical frequency associated with said phase shift value φ as a function of time and of the temperature of the composition,
- a5) drawing the first chart by means of the measurements performed in stage a1) and of the critical frequency determined in stage a4).

4. A method as claimed in claim 3 wherein, in stage a4), the critical frequency curve is adjusted by means of a parameterized equation from a circuit equivalent to a resistor mounted in parallel with a capacitor.

5. A method as claimed in claim 3 wherein, in stage b), the following stages are carried out:
- b1) measuring the progress of the polymerization reaction of the composition as a function of time and of the temperature of the composition,
- b2) measuring the time left before gelation of the composition as a function of the progress of the polymerization reaction of the composition and of the temperature of the composition,
- b3) drawing the second chart with the measurements obtained in stages b1) and b2).

6. A method as claimed in claim 3 wherein, in stage c), the following stages are carried out:
- c1) measuring the complex impedance of the sample as a function of the frequency of the electric potential at the time t1,
- c2) by means of the measurements of stage c1), determining the critical frequency associated with said value φ of the phase shift between the electric potential and the current,
- c3) measuring the temperature T of the sample at the time t1.

7. A method as claimed in claim 5 wherein, in at least one of stages a1 and b6, the progress of the polymerization reaction is measured by means of one of the following methods: differential enthalpy, infrared spectroscopy, steric-exclusion chromatography and NMR.

8. A method as claimed in claim 5 wherein, in stage b2), the gelation of the composition is determined by rheology.

9. A method as claimed in claim 1, wherein said phase shift value φ is −45°.

10. Use of the method as claimed in claim 1 for determining the time left before gelation of a tubular preform pre-impregnated with a polymerizable resin, the preform being intended to be fed into an oil well, then to be applied against the well walls by radial deformation.

11. A method as claimed in claim 1 wherein, in stage b), the following stages are carried out:
- b1) measuring the progress of the polymerization reaction of the composition as a function of time and of the temperature of the composition,
- b2) measuring the time left before gelation of the composition as a function of the progress of the polymerization reaction of the composition and of the temperature of the composition,
- b3) drawing the second chart with the measurements obtained in stages b1) and b2).

12. A method as claimed in claim 11 wherein, in stage c), the following stages are carried out:
- c1) measuring the complex impedence of the sample as a function of the frequency of the electric potential at the time t1,
- c2) by means of the measurements of stage c1), determining the critical frequency associated with said value φ of the phase shift between the electric potential and the current,
- c3) measuring the temperature T of the sample at the time t1.

13. A method as claimed in claim 1 wherein, in stage c), the following stages are carried out:
- c1) measuring the complex impedance of the sample as a function of the frequency of the electric potential at the time t1,
- c2) by means of the measurements of stage c1), determining the critical frequency associated with said value φ of the phase shift between the electric potential and the current,
- c3) measuring the temperature T of the sample at the time t1.

14. A method as claimed in claim 5 wherein, in stage c), the following stages are carried out:
- c1) measuring the complex impedance of the sample as a function of the frequency of the electric potential at the time t1,
- c2) by means of the measurements of stage c1), determining the critical frequency associated with said value φ of the phase shift between the electric potential and the current,
- c3) measuring the temperature T of the sample at the time t1.

* * * * *